US010228345B2

(12) United States Patent
Lei et al.

(10) Patent No.: US 10,228,345 B2
(45) Date of Patent: Mar. 12, 2019

(54) HIGH TEMPERATURE SENSOR FOR REDUCING GAS

(71) Applicant: University of Connecticut, Farmington, CT (US)

(72) Inventors: Yu Lei, Mansfield Center, CT (US); Yixin Liu, Willimantic, CT (US)

(73) Assignee: University of Connecticut, Farmington, CT (US)

( * ) Notice: Subject to any disclaimer, the term of this patent is extended or adjusted under 35 U.S.C. 154(b) by 329 days.

(21) Appl. No.: 14/903,497

(22) PCT Filed: Jul. 11, 2014

(86) PCT No.: PCT/US2014/046305
§ 371 (c)(1),
(2) Date: Jan. 7, 2016

(87) PCT Pub. No.: WO2015/006664
PCT Pub. Date: Jan. 15, 2015

(65) Prior Publication Data
US 2016/0169836 A1 Jun. 16, 2016

Related U.S. Application Data

(60) Provisional application No. 61/845,713, filed on Jul. 12, 2013.

(51) Int. Cl.
*G01N 27/416* (2006.01)
*G01N 27/30* (2006.01)
(Continued)

(52) U.S. Cl.
CPC ....... *G01N 27/4166* (2013.01); *G01N 27/026* (2013.01); *G01N 27/304* (2013.01);
(Continued)

(58) Field of Classification Search
CPC .............. G01N 27/026; G01N 27/301; G01N 27/4166; G01N 27/403; G01N 27/127;
(Continued)

(56) References Cited

U.S. PATENT DOCUMENTS 7,775,083 B2   8/2010   Potyrailo et al.
2010/0147684 A1   6/2010   Park et al.

OTHER PUBLICATIONS

Khodadadi et al. Sensors and Actuators B, 2001, 267-271 (Year: 2001).*

(Continued)

*Primary Examiner* — Gurpreet Kaur
(74) *Attorney, Agent, or Firm* — McCarter & English, LLP

(57) ABSTRACT

The present disclosure provides improved sensor assemblies for gases. More particularly, the present disclosure provides for gas sensor assemblies operating at high temperature. Improved high temperature sensor assemblies for reducing gas are provided. In some embodiments, the present disclosure provides advantageous impedancemetric high temperature gas sensor assemblies based on electrospun nanofibers and having selectivity towards reducing gas, and related methods of use. In exemplary embodiments, the present disclosure provides for impedancemetric high temperature gas sensor assemblies having selectivity towards reducing gas. In certain embodiments, the sensor assembly includes electrospun nanofibers. Impedancemetric techniques have been employed at high operating frequency (e.g., $10^5$ Hz) for the first time to provide real-time assemblies, methods and devices to sensitively and/or selectively detect reducing gas (e.g., CO, $C_3H_8$ (propane), etc.) at high temperatures (e.g., at about 800° C.).

22 Claims, 8 Drawing Sheets

(51) Int. Cl.
  *G01N 33/00* (2006.01)
  *G01N 27/02* (2006.01)
(52) U.S. Cl.
  CPC ....... *G01N 33/004* (2013.01); *G01N 33/0037* (2013.01); *G01N 33/0042* (2013.01); *Y02A 50/245* (2018.01)
(58) Field of Classification Search
  CPC ............. G01N 33/0037; G01N 33/004; G01N 33/0042; G01N 33/0044
  See application file for complete search history.

(56) References Cited

OTHER PUBLICATIONS

Wu et al., Sensors and Actuators B, 110, 2005, 49-53. (Year: 2005).*
Tang et al., Fabrication of Pt/CeO2 Nanofibers for Use in Water-Gas Shift Reaction, Material Letters, Mar. 5, 2012, vol. 77, pp. 7-9.
Zhi et al., Electrospun La0.8Sr0.2MnO3 nanofibers for a high-temperature electrochemical carbon monoxide sensor, Nanotechnology, Jul. 2, 2012, vol. 23, pp. 305501, 1-6.
Liu et al., CeO2 Nanofibers for In Situ O2 and CO Sensing in Harsh Environments, RSC Advances, Apr. 3, 2012, vol. 2, pp. 5193-5198.
PCT International Search Report and Written Opinion for PCT/US2014/046305 dated Oct. 23, 2014.
PCT/US2014/043605, filed Jul. 11, 2014, WO 2015/006664.
U.S. Appl. No. 61/845,713, filed Jul. 12, 2013.

* cited by examiner

HIGH TEMPERATURE SENSOR FOR REDUCING GAS

CROSS-REFERENCE TO RELATED APPLICATIONS

This application claims the benefit of U.S. Provisional Application No. 61/845,713 filed Jul. 12, 2013, all of which is herein incorporated by reference in its entirety.

RELATED FEDERALLY SPONSORED RESEARCH

This invention was made with government support under Grant No. DE-FE0000870 awarded by the U.S. Department of Energy. The government has certain rights in the invention.

BACKGROUND

1. Technical Field

The present disclosure relates to sensor assemblies for gases and, more particularly, to gas sensor assemblies operating at high temperature.

2. Background Art

In general, the selectivity of a gas sensor is a persistent challenge for most exhausted gas sensors. Currently, potentiometric oxygen sensors based on zirconia are generally the only reasonably successful commercial high temperature sensors which can work above 800° C. Only limited reports are on reducing gas detection at high temperatures (e.g., 800-1000° C.). Other than stability and sensitivity of a sensor at high temperature, selectivity is a challenging issue.

Thus, an interest exists for improved sensor assemblies for gases. These and other inefficiencies and opportunities for improvement are addressed and/or overcome by the assemblies, systems and methods of the present disclosure.

SUMMARY

The present disclosure provides improved sensor assemblies for gases. More particularly, the present disclosure provides for gas sensor assemblies operating at high temperature.

In exemplary embodiments, the present disclosure provides advantageous high temperature sensor assemblies for reducing gas. In certain embodiments, the present disclosure provides impedancemetric high temperature gas sensor assemblies based on electrospun nanofibers and having selectivity towards reducing gas, and related methods of use.

Disclosed herein are exemplary impedancemetric high temperature gas sensor assemblies having selectivity towards reducing gas. In certain embodiments, the sensor assembly includes electrospun nanofibers.

As disclosed herein, impedancemetric techniques have been employed at high operating frequency (e.g., $10^5$ Hz) for the first time to provide real-time assemblies, methods and devices to sensitively and/or selectively detect reducing gas (e.g., CO, $C_3H_8$ (propane), etc.) at high temperatures (e.g., at about 800° C.).

The present disclosure provides for an impedancemetric sensor assembly including a substrate; one or more electrodes positioned on the substrate; a plurality of electrospun nanofibers positioned on the substrate; wherein the sensor assembly is adapted to operate at a temperature of about 500° C. or more and a frequency of about 100 kHz or more to detect a gas.

The present disclosure also provides for an impedancemetric sensor assembly wherein the detected gas is CO or $C_3H_8$. The present disclosure also provides for an impedancemetric sensor assembly wherein the sensor assembly is adapted to operate at a temperature of from about 800° C. to about 1000° C. to detect the gas.

The present disclosure also provides for an impedancemetric sensor assembly wherein the sensor assembly is adapted to operate at a frequency of from about 100 kHz to about 1 MHz to detect the gas. The present disclosure also provides for an impedancemetric sensor assembly wherein the sensor assembly is adapted to operate to provide real-time detection of the gas.

The present disclosure also provides for an impedancemetric sensor assembly wherein the plurality of electrospun nanofibers include Pt—$CeO_2$ nanofibers. The present disclosure also provides for an impedancemetric sensor assembly wherein the plurality of electrospun nanofibers are configured and adapted to have high thermal stability and the sensor assembly has high sensitivity toward strong reducing gases.

The present disclosure also provides for an impedancemetric sensor assembly wherein there is substantially no interference from $O_2$, $CO_2$, NO or $SO_2$ at the operating frequency selected for detection of CO or $C_3H_8$.

The present disclosure also provides for an impedancemetric sensor assembly wherein the sensor assembly is adapted to operate in a dynamic flow system to detect the gas. The present disclosure also provides for an impedancemetric sensor assembly wherein the plurality of electrospun nanofibers include $CeO_2$ nanofibers doped with material selected from the group consisting of noble metals, metal oxides, semi-conducting metal oxides, pervoskites, pervoskite structures and combinations thereof.

The present disclosure also provides for a method for fabricating an impedancemetric sensor assembly including: a) providing a substrate; b) positioning one or more electrodes on the substrate; c) positioning a plurality of electrospun nanofibers on the substrate to form a sensing assembly; d) operating the sensing assembly at a temperature of about 500° C. or more and a frequency of 100 kHz or more to detect a gas.

The present disclosure also provides for a method for fabricating an impedancemetric sensor assembly wherein prior to step c), the plurality of electrospun nanofibers are fabricated by: (i) electrospinning $H_2PtCl_6$—$Ce(NO_3)_3$-PVP precursor nanofibers, and (ii) calcinating the electrospun precursor nanofibers to generate a plurality of electrospun Pt—$CeO_2$ nanofibers.

The present disclosure also provides for a method for fabricating an impedancemetric sensor assembly wherein calcinating the electrospun precursor nanofibers includes: (i) calcinating the electrospun precursor nanofibers during a first calcination step at about 500° C. for about 3 hours, and (ii) calcinating the electrospun precursor nanofibers during a second subsequent calcination step at about 1000° C. for about 3 hours to generate the plurality of electrospun Pt—$CeO_2$ nanofibers.

The present disclosure also provides for a method for fabricating an impedancemetric sensor assembly wherein the detected gas is CO or $C_3H_8$.

The present disclosure also provides for a method for fabricating an impedancemetric sensor assembly wherein the sensing assembly is operated at a temperature of from about 800° C. to about 1000° C. to detect the gas. The present disclosure also provides for a method for fabricating an impedancemetric sensor assembly wherein the sensing assembly is operated at a frequency of from about 100 kHz to about 1 MHz to detect the gas.

The present disclosure also provides for a method for fabricating an impedancemetric sensor assembly wherein the plurality of electrospun nanofibers include Pt—$CeO_2$ nanofibers.

The present disclosure also provides for a method for fabricating an impedancemetric sensor assembly wherein the plurality of electrospun nanofibers include $CeO_2$ nanofibers doped with material selected from the group consisting of noble metals, metal oxides, semi-conducting metal oxides, pervoskites, pervoskite structures and combinations thereof.

The present disclosure also provides for a method for fabricating nanofibers including electrospinning $H_2PtCl_6$—$Ce(NO_3)_3$-PVP precursor nanofibers; and calcinating the electrospun precursor nanofibers to generate a plurality of electrospun Pt—$CeO_2$ nanofibers.

The present disclosure also provides for a method for fabricating nanofibers wherein calcinating the electrospun precursor nanofibers includes: (i) calcinating the electrospun precursor nanofibers during a first calcination step at about 500° C. for about 3 hours, and (ii) calcinating the electrospun precursor nanofibers during a second subsequent calcination step at about 1000° C. for about 3 hours to generate the plurality of electrospun Pt—$CeO_2$ nanofibers.

The present disclosure also provides for a method for fabricating nanofibers wherein the plurality of electrospun Pt—$CeO_2$ nanofibers are configured and adapted to have high thermal stability and wherein a sensor assembly including a portion of the generated electrospun Pt—$CeO_2$ nanofibers has high sensitivity toward strong reducing gases.

Any combination or permutation of embodiments is envisioned. Additional advantageous features, functions and applications of the disclosed assemblies, systems and methods of the present disclosure will be apparent from the description which follows, particularly when read in conjunction with the appended figures. References, publications and patents listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various steps, features and combinations of steps/features described below and illustrated in the figures can be arranged and organized differently to result in embodiments which are still within the spirit and scope of the present disclosure. To assist those of ordinary skill in the art in making and using the disclosed systems, assemblies and methods, reference is made to the appended figures, wherein:

FIGS. 1A-1B show SEM images of: (FIG. 1A) Pt—$CeO_{2(500)}$ NFs (obtained after calcination of precursor nanofibers at 500° C.), and (FIG. 1B) Pt—$CeO_{2(1000)}$ NFs (obtained after Pt—$CeO_{2(500)}$ was further calcined at 1000° C.); FIGS. 1C-1D show the EDX spectra of: (FIG. 1C) the point on one selected Pt—$CeO_{2(1000)}$ nanofiber, and (FIG. 1D) the point on one selected nanoparticle; FIG. 1E shows XRD patterns of Pt—$CeO_{2(1000)}$ NFs;

(FIG. 2A) sketch of the Pt—$CeO_2$ NFs based sensor; (FIG. 2B) equivalent circuit model for the sensor; (FIG. 2C) impedance spectra (dots) and fitted curves (lines) of the sensor in $N_2$ and different concentrations of $O_2$; and (FIG. D) impedance spectra (dots) and fitted curves (lines) of the sensor in different concentrations of CO;

(FIG. 4A) real-time selectivity study on resistor-type Pt—$CeO_2$ NFs-based sensor towards $O_2$ and CO at an applied DC bias of 1V at 800° C.; (FIG. 4B) real-time selectivity study on impedancemetric Pt—$CeO_2$ NFs-based sensor towards $O_2$ and CO, operating at 100 kHz with amplitude of 0.5 V at 800° C.; (FIG. 4C) summarized sensitivity/selectivity of the impedancemetric sensor and resistor-type sensor in different gases ($N_2$, $O_2$, CO, NO, $CO_2$ and $SO_2$);

(FIG. 5A) real-time CO detection of the Pt—$CeO_2$ NFs-based sensor at an operating frequency of 100 kHz with amplitude of 0.5 V at 800° C.; (FIG. 5B) calibration curve for CO responses;

(FIG. 6A) impedance spectra (Bode-plots) of Pt—$CeO_2$ NFs based sensor in $N_2$, 1% $O_2$ and $C_3H_8/N_2$ in varied concentrations; (FIG. 6B) real-time $C_3H_8$ detection of the Pt—$CeO_2$ NFs-based sensor at an operating frequency of 100 kHz with amplitude of 0.5 V at 800° C.; (FIG. 6C) calibration curve for $C_3H_8$ responses;

(FIG. 7A) impedance spectra (Nyquist plots) of Pt—$CeO_2$ NFs based sensor in gas mixtures including NO, $CO_2$ and $SO_2$ balanced by $N_2$, and (FIG. 7B) $C_3H_8$ balanced by $N_2$ from 0.1 Hz to 1 MHz with amplitude of 0.5 V at 800° C. (inset is the spectra of 80 ppm and 100 ppm $C_3H_8$ in large scale)

DETAILED DESCRIPTION

Figures 1A, 1B, 1C, 1D, 1E:
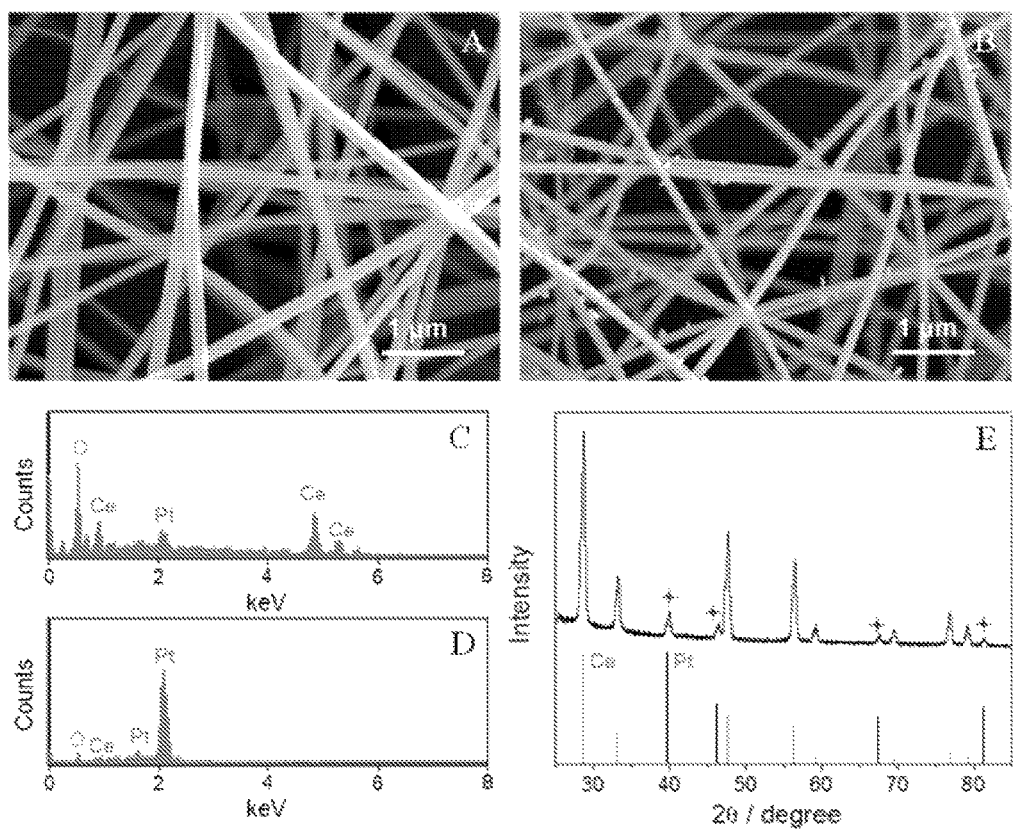

The exemplary embodiments disclosed herein are illustrative of advantageous sensor assemblies for gases (e.g., high temperature sensor assemblies for reducing gas), and systems of the present disclosure and methods/techniques thereof. It should be understood, however, that the disclosed embodiments are merely exemplary of the present disclosure, which may be embodied in various forms. Therefore, details disclosed herein with reference to exemplary systems/assemblies and associated processes/techniques of assembly and use are not to be interpreted as limiting, but merely as the basis for teaching one skilled in the art how to make and use the advantageous systems, assemblies and methods of the present disclosure.

The present disclosure provides improved sensor assemblies for gases. More particularly, the present disclosure provides for gas sensor assemblies operating at high temperature.

In general, the present disclosure provides improved high temperature sensor assemblies for reducing gas. In some embodiments, the present disclosure provides advantageous impedancemetric high temperature gas sensor assemblies based on electrospun nanofibers and having selectivity towards reducing gas, and related methods of use.

The present disclosure provides for impedancemetric high temperature gas sensor assemblies having selectivity towards reducing gas. In certain embodiments, the sensor assembly includes electrospun nanofibers.

As disclosed herein, impedancemetric techniques have been employed at high operating frequency (e.g., $10^5$ Hz) for the first time to provide real-time assemblies, methods and devices to sensitively and/or selectively detect reducing gas (e.g., CO, $C_3H_8$ (propane), etc.) at high temperatures (e.g., at about 800° C.).

Current practice provides that the selectivity of a gas sensor is a persistent challenge for most exhausted gas sensors. Researchers are trying to fabricate new materials with high selectivity; to design sensing device configurations to include a filter or physical layer; and to use new sensing technology. In exemplary embodiments, the present disclosure provides for impedancemetric high temperature gas sensor assemblies having selectivity towards reducing gas, thereby providing a significant commercial, manufacturing and/or operational advantage as a result.

Disclosed herein is a facile approach to synthesize a highly porous nanomaterial (e.g., Pt—$CeO_2$ nanofibers) with strong thermal stability and high sensitivity toward strong reducing gases (e.g., CO and $C_3H_8$) at high temperature (e.g., about 800° C.). Exemplary sensing devices/assemblies of the present disclosure are easily fabricated and cost-effective. By measuring the impedance of the sensor at high frequency (e.g., $10^5$ Hz), the interference from other gases (e.g., $O_2$, $CO_2$, NO, $SO_2$) can be significantly minimized. The exemplary impedancemetric sensors disclosed herein can have a simple configuration, good stability, high sensitivity and selectivity toward CO and/or $C_3H_8$.

As the most common type of harsh environment sensors, high temperature gas sensors are of importance to improve combustion efficiency and/or control emissions. Incomplete combustion of fossil fuels, which play a dominant role as a primary energy source for automotive and power industries, leads to the emission of carbon monoxide and hydrocarbon gas. In order to reduce the pollutant emissions and to improve the combustion efficiency, high temperature gas sensors that can provide feedback in real time to combustion processes and monitor emissions are in high demand. There is a current unmet need for such sensors.

On-Board-Diagnostic (OBD) systems usually require gas sensors that can operate in harsh environments at above 500° C., and in close proximity to engines where the exhaust gases can reach temperatures close to 1000° C. To date, commercially available sensor technology for high temperature is extremely limited due to the high requirements for sensing materials and sensor performance.

The detection approach referred to as "impedancemetric," which employs AC measurements at a specified frequency, has drawn attention recently. The approach is related to solid-state impedance spectroscopy which is an electrochemical characterization technique that measures the cell response over a range of frequencies, typically from sub-hertz to megahertz. Impedancemetric techniques have been applied on both solid-electrolyte-based sensors and resistor-type sensors. Most of the known impedancemetric sensors operate at low frequency (e.g., less than 100 Hz) because impedance spectra of different concentrations of analyte gas overlap in the high frequency range and the sensors can only get responses at low frequency.

For certain exemplary sensors disclosed herein, resistor-type configurations are used and provide advantages, such as simple configuration, easy fabrication, cost effectiveness and ready miniaturization capability. Disclosed herein for the first time is a high temperature gas sensor successfully operated at high frequency (e.g., 100 kHz), which can selectively detect reducing gas (e.g., CO and $C_3H_8$) with good stability, sensitivity and reproducibility.

In exemplary embodiments and to fabricate a novel material disclosed herein, Pt decorated $CeO_2$ nanofibers (NFs) were fabricated by electrospinning of $H_2PtCl_6$—Ce$(NO_3)_3$-PVP (molar ratio, 5% Pt) precursor nanofibers, followed by two-step calcination. The precursor nanofibers were first calcined at 500° C. for 3 hours to remove the polymer matrix and generate Pt—$CeO_{2(500)}$ NFs, the morphology of which was characterized by SEM, as shown in FIG. 1A. The nanofibers were uniform and well-distributed with an average diameter of 177±17 nm. After calcination at 1000° C. for another 3 hours, the average diameter of the nanofibers slightly shrank to 138±14 nm, and compared to the smooth surface of Pt—$CeO_{2(500)}$ NFs, nanoparticles of an average diameter of 85±25 nm emerged on the surface of the Pt—$CeO_{2(1000)}$ NFs. The X-ray energy dispersive spectroscopy (EDX) point analysis was employed to investigate the compositions of the nanofibers and nanoparticles on the surface. FIG. 1C presents the EDX spectrum on one point of a random selected Pt—$CeO_{2(1000)}$ nanofiber, indicating the presence of Ce, Pt and oxygen in the nanofiber matrix. In the contrary, from the point EDX spectrum of a random selected nanoparticle (FIG. 1D), one can see that the nanoparticles on the nanofibers surface is mainly composed of Pt and barely Ce and oxygen signals can be observed. These results imply that Pt migrated from the nanofibers to the surface to form Pt nanoparticles during the calcination process at 1000° C., which is also responsible for the reduced diameter of the nanofibers. XRD was carried out to further characterize the composition and crystal structure of as-prepared Pt—$CeO_{2(1000)}$ NFs. As shown in FIG. 1E, the XRD spectrum of Pt—$CeO_2$ NFs matches the combination of the standard spectra of $CeO_2$ and Pt, which revealed the formation of $CeO_2$ and Pt after calcination.

Figures 2A, 2B, 2C, 2D:
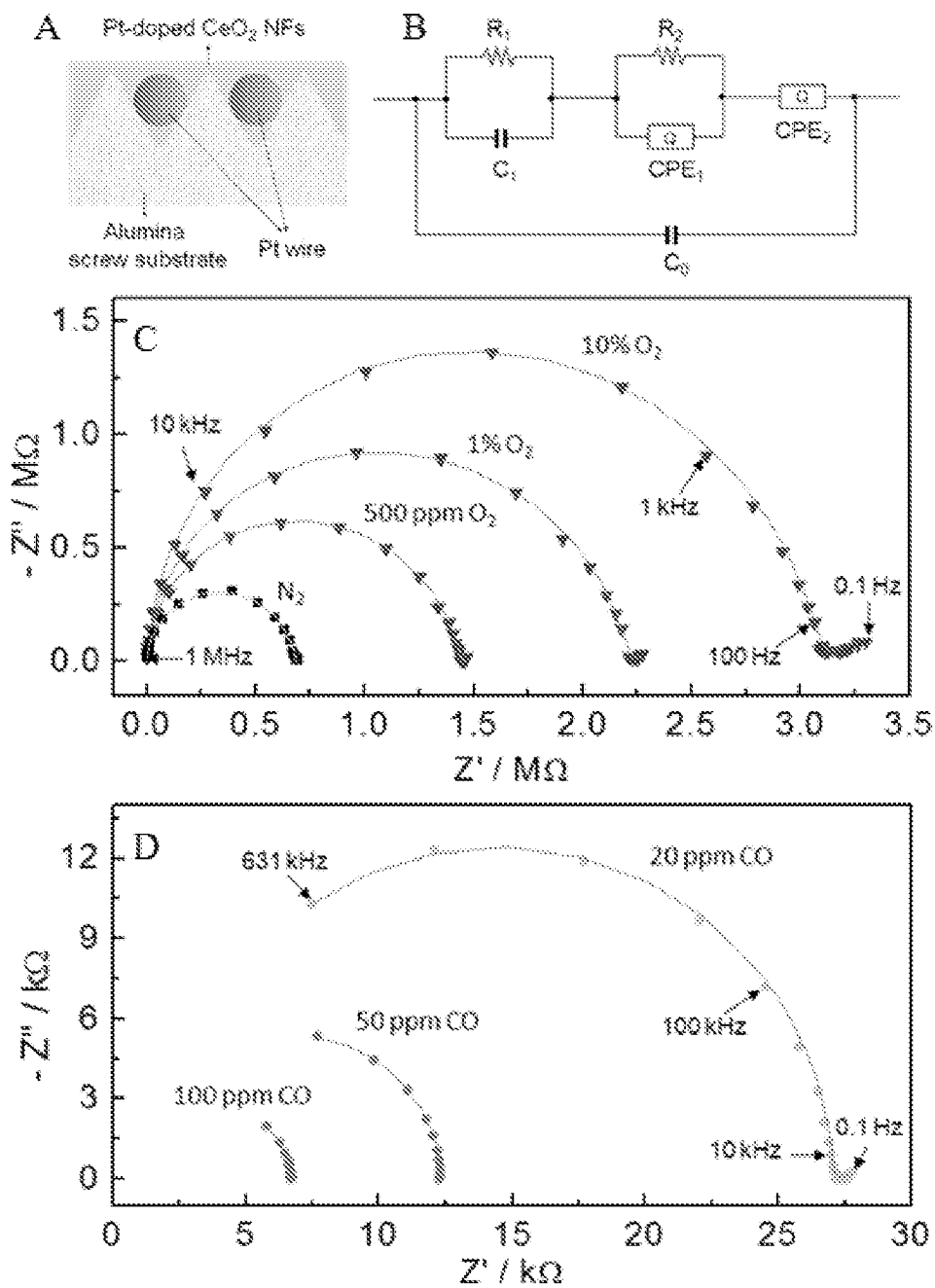
FIGS. 2A-2D show.

The as-prepared Pt—$CeO_{2(1000)}$ NFs were then employed as the sensing material to fabricate a sensor on an $Al_2O_3$ ceramic screw in the resistor-type configuration using two Pt wires as two electrodes, as shown in FIG. 2A. The Pt—$CeO_2$ NFs-based sensor was operated in a dynamic flow system at about 800° C. for the in-situ high temperature gas sensing.

Complex impedance measurement was first performed on the Pt—$CeO_2$ NFs-based sensor. FIGS. 2C and 2D show the Nyquist plots (data dots) obtained from the sensor at 800° C. in high purity $N_2$ and in the gas mixture with different concentrations of $O_2$ and CO balanced by $N_2$. One can see from FIG. 2C that a large and slightly depressed semicircular arc with a small tail can be observed in $N_2$, as well as in different concentrations of $O_2$ mixture in the examined frequency range (e.g., 0.1 Hz-1 MHz). With increasing concentrations of $O_2$, the radius of the semicircular arc greatly increased, implying the sensor is very sensitive to $O_2$. The impedance spectra in different concentrations of $SO_2$, $CO_2$ and NO were also measured, which are very similar to the one of $N_2$, as shown in Table 51 below. $CO_2$ and NO showed weak oxidizing property, while $SO_2$ exhibited a weak reducing behavior; and the sensor only showed limited sensitivity towards these three gases. From FIG. 2D, one can notice that the impedance magnitude |Z| of the sensor in CO/$N_2$ mixture dramatically dropped by 2 decades and the shape of the spectra also shrank to only a portion of the semicircular arc, which indicates CO is a strong reducing gas and the Pt—$CeO_2$ NFs are extremely sensitive to CO.

Equivalent circuit analysis was conducted to better understand the sensing mechanism. FIG. 2B presents the equivalent circuit model for the Pt—$CeO_2$ NFs-based sensor. A RC-parallel element ($R_1 \| C_1$) corresponds to the bulk Pt—$CeO_2$ NFs. $R_1$ represents the resistance of bulk Pt—$CeO_2$ NFs, and $C_1$ is related to the dielectric properties of the material. The following element $((R_2\|CPE_1)+CPE_2)$ in series is used to describe the interface between sensing material and Pt electrodes. $R_2$ represents the charge transfer resistance at the interface. A constant phase element $CPE_1$ is used to account for the non-ideal behavior of the double layer at the interface due to the porosity, surface roughness, etc. The low-frequency Warburg-like contribution is described by $CPE_2$, which is associated with gas diffusion. To accomplish the model, a parallel capacitor ($C_0$) is applied to stand for the capacity of the substrate. Due to the time constants of RC-parallel element ($R_1\|C_1$) and RQ-parallel element ($R_2\|CPE_2$) are close to each other, they both contribute to the large arc. The small tail following the large arc can be ascribed to gas diffusion, corresponding to $CPE_2$. The value of $C_0$ was determined by simulation of the device without Pt—$CeO_2$ NFs.

Based on the reports on double layer capacitance, the dielectric constants in the double-layers have roughly the same value with varied concentration of oxygen vacancies. Therefore, $n_1$ in $CPE_1$, which is related to the dielectric constants in the double layer capacitance, was also set as a constant of 0.8 to fit the experimental data due to the large number of variables. For the diffusion related $CPE_2$ which is responsible for the tail in low frequency range, $n_2$ was set as constant of 0.1 except the cases of $O_2$ with different concentrations. Under these pre-selected constants, this equivalent circuit model gives a very good approximation of the experimental results. As shown in FIGS. 2C and 2D, the solid lines are the fitting curves which are in a good agreement with the experiment data dots. The parameters of the model for the fitting curves in different gas atmospheres are listed in Table S1 below.

From the fitting parameters, it is concluded that both of the resistance of bulk Pt—$CeO_2$ NFs and the interface charge transfer resistance contribute a lot to the change of the impedance spectra. In addition, the sum of the fitting values of $R_1$ and $R_2$ is very close to the measured resistance of the sensor device in different gas atmosphere (which can be presented as the diameter of the large arc), further indicating the reliability of the fitting values in the equivalent circuit model and the appropriateness of the pre-selected constant values. $CeO_2$ is an n-type semiconductor and the predominant point defects in $CeO_2$ are the electron trapped by lattice Ce and oxygen vacancy. The reaction for the formation of ionic and electronic charge carriers can be written as:

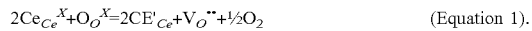

$$2Ce_{Ce}^X + O_O^X = 2CE'_{Ce} + V_O^{\cdot\cdot} + \tfrac{1}{2}O_2 \quad \text{(Equation 1).}$$

Upon the exposure to $O_2$, oxygen can incorporate with electrons and oxygen vacancy to form lattice oxygen, leading to the increased resistance $R_1$ and reduced capacitance $C_1$. It was reported that the capacitance of $CeO_2$ decreases with increasing oxygen partial pressure, which is in good agreement with the fitting data. After introducing CO to the sensing atmosphere, CO will extract lattice oxygen to form $CO_2$, which will generate oxygen vacancies and electrons according to Equation 1. Due to the increasing concentration of electrons, both material bulk resistance $R_1$ and charge transfer resistance $R_2$ dramatically decrease. The oxygen depletion also results in an increase in the capacitance $C_1$. The fitting parameters of weak oxidizing gas $CO_2$ and NO show the same trend as $O_2$; while weak reducing gas $SO_2$ behaved like CO.

Figure 3:
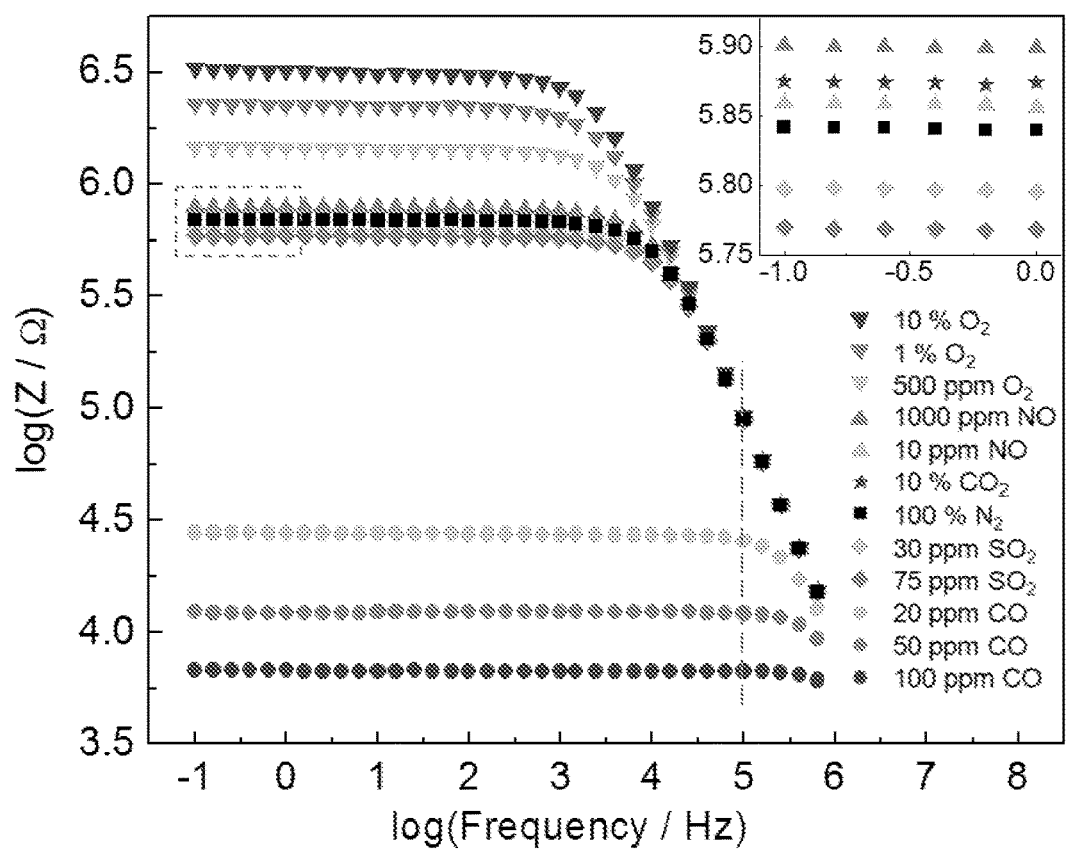
FIG. 3 shows impedance spectra (Bode-plots) of Pt—$CeO_2$ NFs based sensor in $N_2$ and different gases ($O_2$, CO, NO, $CO_2$ and $SO_2$ balanced by $N_2$) with varied concentrations; the inset shows the plots in the dashed box in large scale.

The impedance spectroscopy data of the sensor in different gas atmospheres can also be presented as Bode plots, where $\log|Z|$ is plotted versus $\log(\text{frequency})$, as shown in FIG. 3. In all cases, with decreasing frequency, the modulus $|Z|$ of the sensor increased and gradually reached their plateau. For 100 ppm CO, $|Z|$ almost kept as a constant in the examined frequency range. For the impedancemetric real-time gas detection, the frequency was fixed, which can be selected based on the Bode plots. In the Bode plots, one takes the spectrum of $N_2$ as the baseline (black square), then the larger the distance is between the targeted gas and $N_2$, then the more sensitive the sensor is towards that targeted gas.

One can see from FIG. 3 that, in the low frequency range, the sensor is sensitive to $O_2$ with increasing modulus and to CO with reducing modulus, and it also shows concentration-dependent behavior for all tested gases. In the high frequency range (>10 kHz), except the CO/$N_2$ mixture, the Bode plots for all other tested gases overlapped with $N_2$, indicating that the sensor is only sensitive to strong reducing gas CO and it has almost no response towards other tested gases.

This is also the reason why most reported impedancemetric sensors operate at low frequency (e.g., less than 100 Hz). However, with increasing frequency (10 kHz), the sensitivity of the sensor towards CO is also reducing. In other words, in order to obtain the selectivity at high frequency, part of the sensitivity towards CO will be sacrificed. Therefore, the optimized operating frequency was selected at 100 kHz, which is high enough to eliminate the interference from tested oxidizing and weak reducing gases (e.g., $O_2$, NO, $SO_2$ and $CO_2$), and low enough to detect strong reducing gas CO with good sensitivity.

Figures 4A, 4B, 4C:
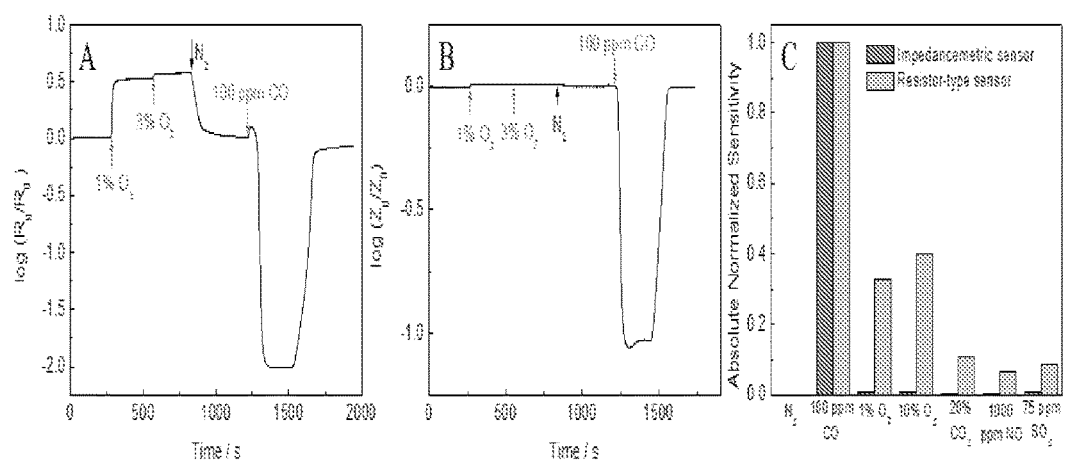
FIGS. 4A-4C show.

A Pt—$CeO_2$ NFs based resistor-type sensor was tested as a comparison in order to verify the improved selectivity of the impedancemetric sensor operating at high frequency. High purity $N_2$ was used as the reference gas. Due to the resistance/modulus of the sensor changes in several orders and in different directions, the sensitivity of the impedancemetric sensor is defined as $\log(Z_g/Z_0)$, where $Z_g$ is the real-time measured modulus upon exposure to different gas mixture and $Z_0$ is the initial modulus in high purity $N_2$; and similarly, the sensitivity of the resistor-type sensor is defined as $\log(R_g/R_0)$. The real-time selectivity study used $O_2$ and CO as demonstration. As shown in FIGS. 4A and 4B, for the resistor-type sensor, 1% $O_2$ introduced 33% interference to the response of 100 ppm CO; while for impedancemetric sensor operating at 100 kHz, $O_2$ only showed a negligible response.

The real-time detection of $CO_2$, NO and $SO_2$ were also performed. At the selected frequency, the sensor barely showed any response towards these gases. The sensitivity of the Pt—$CeO_2$ NFs-based impedancemetric sensor and resistor-type sensor towards different gases is summarized in FIG. 4C. To compare the sensitivity of both reducing and oxidizing gas, the absolute sensitivity was used. As presented in FIG. 4C, the resistor-type sensor suffered from significant interference from high concentration of oxygen and other gaseous species, while the impedance sensor exhibited good sensitivity and selectivity toward CO at the selected operating frequency of 100 kHz, suggesting that the developed impedancemetric sensor operated at high frequency, and is a very promising sensor toward selective strong reducing gas detection at about 800° C.

Figures 5A, 5B:
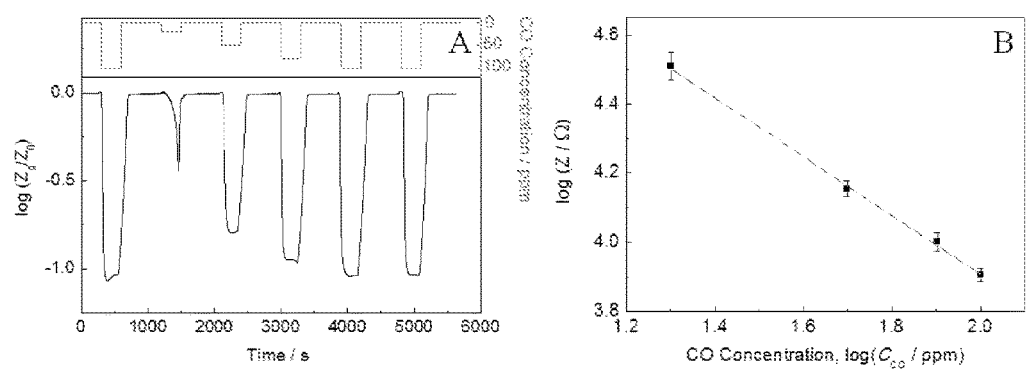
FIGS. 5A-5B show.
Figure 8:
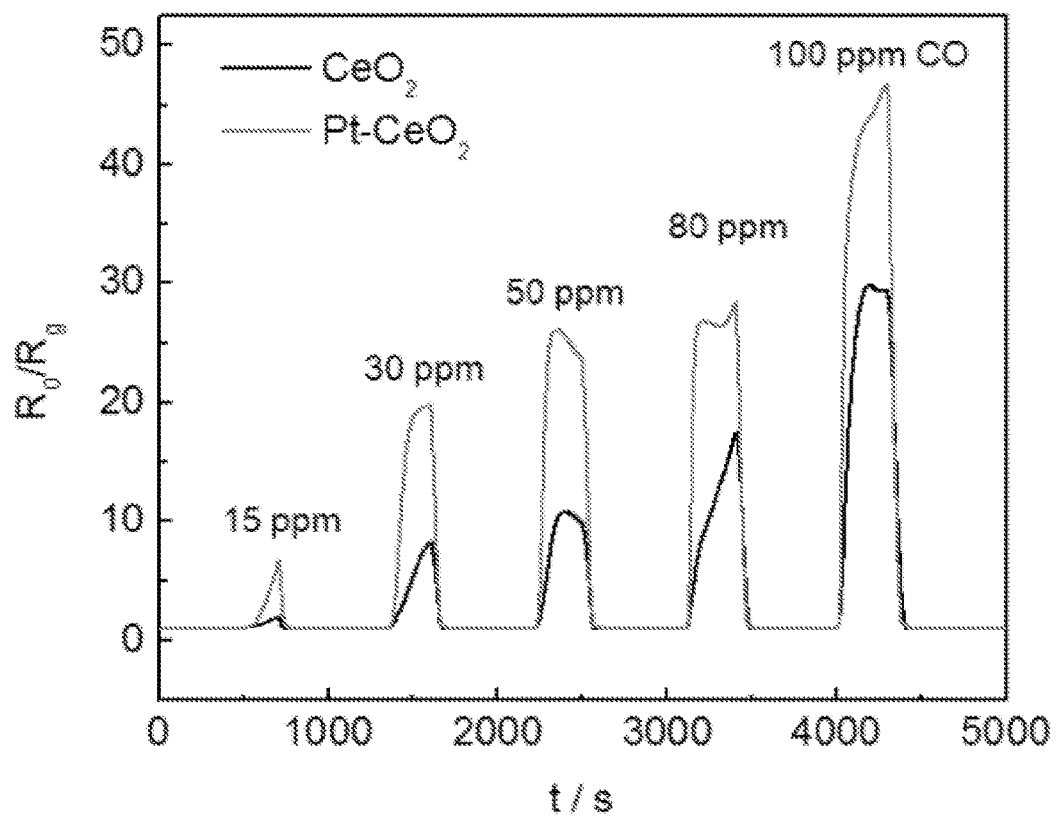
FIG. 8 shows a comparison of real-time CO detection of the $CeO_2$ NFs and Pt—$CeO_2$ NFs based sensors at 800° C.; $R_0$ is the initial resistance of the sensors in $N_2$ and $R_g$ is the real-time resistance in different gas mixtures.

The real-time CO detection of a Pt—$CeO_2$ NFs-based impedancemetric sensor was carried out at high operating temperature of 800° C. with a fixed frequency of 100 kHz. FIG. 5A represents typical impedance modulus responses of the sensor as a function of time upon periodic exposure to CO (with concentrations from 20 ppm to 100 ppm) balanced in high purity $N_2$. The sensor showed good sensitivity at the operating frequency of 100 kHz towards CO. Upon exposure to 100 ppm CO, the modulus of the sensor quickly drops and is 10 times smaller than the |Z| in $N_2$. The response time ($t_{90}$) of the sensor towards 100 ppm CO is 50 seconds, which is defined as the time when the change of |Z| reached 90% of the maximum response after exposure to CO. The actual response time should be much faster considering the time required for the gas to fill the test chamber. The response of the sensor towards CO can be substantially completely recovered by $N_2$ and the sensor responses towards three-time exposure of 100 ppm CO showed good reproducibility with a small relative standard deviation (RSD) of 0.5%. A comparison study of resistor-type sensor using $CeO_2$ NFs indicates that the presence of Pt in Pt—$CeO_2$ NFs could significantly improve the sensing performance toward CO detection. The response of Pt—$CeO_2$ NFs toward 50 ppm CO is almost three-fold that of $CeO_2$ NFs, as shown in FIG. 8. The CO concentration dependent behavior was revealed by the calibration curve presented in FIG. 5B, which shows a linear relationship between log|Z| and log $C_{CO}$ (concentration of CO).

Figures 6A, 6B, 6C:
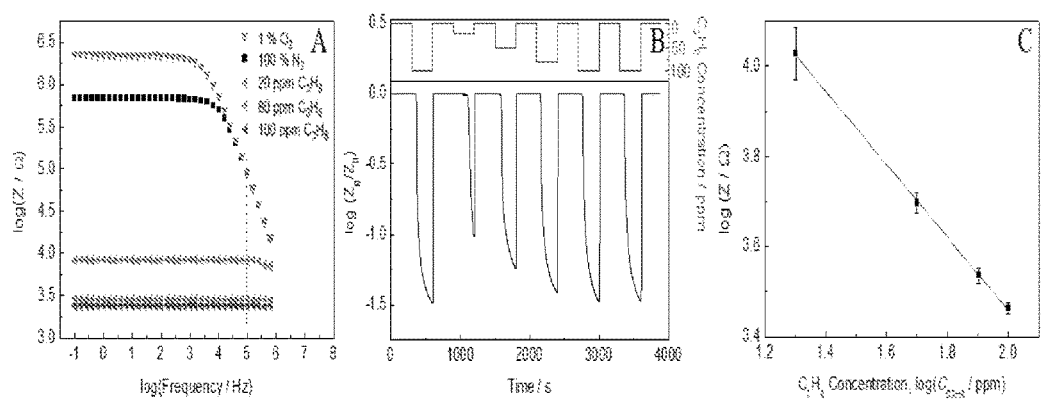
FIGS. 6A-6C show.
Figures 7A, 7B:
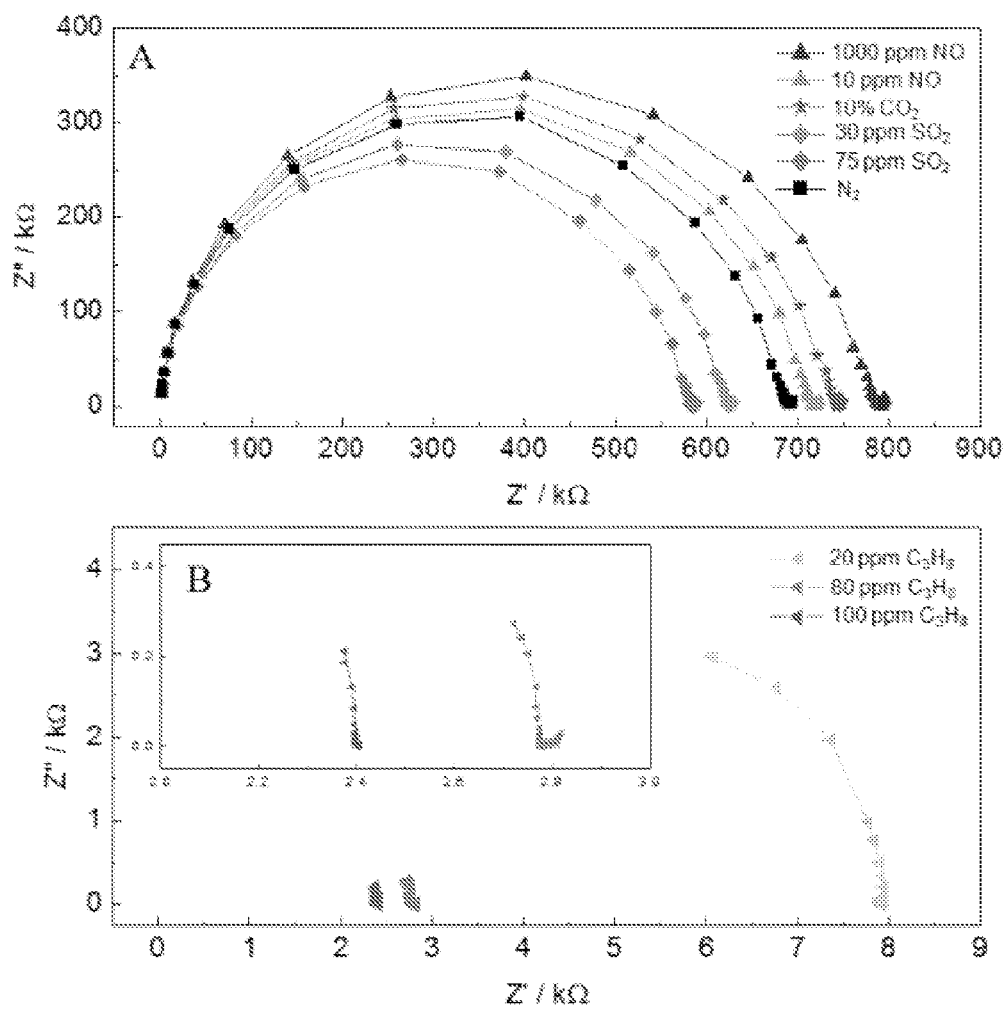
FIGS. 7A-7B show.

To further verify the idea, another strong reducing gas from the hydrocarbon group, propane, was tested as demonstration. Impedance spectra of the Pt—$CeO_2$ NFs-based sensor towards different concentration of $C_3H_8$ balanced in $N_2$ were first measured. Nyquist plots are shown in FIG. 7B which only exhibits very short curves for 80 and 100 ppm $C_3H_8$, indicating the sensor is even more sensitive to $C_3H_8$. FIG. 6A shows the Bode plots of three concentrations of $C_3H_8$ and $N_2$ and 1% $O_2$ as comparison, referring to FIG. 3. At 100 kHz, the sensor showed good sensitivity towards $C_3H_8$ and substantially no response towards 1% $O_2$. Due to the strong reducing property of $C_3H_8$, the sensor cannot be fully recovered by high purity $N_2$. Therefore, 1% $O_2$ was chosen as recovering gas, since there is substantially no difference of the baseline in $N_2$ and 1% $O_2$.

FIG. 6B presents the real-time $C_3H_8$ detection at operated frequency of 100 kHz at 800° C. The sensor exhibited excellent sensitivity towards 100 ppm $C_3H_8$, indicated by the fact that the modulus of the sensor quickly drops 30 times smaller than the modulus in 1% $O_2$. The recovery of the sensor from exposure to $C_3H_8$ by 1% $O_2$ is very fast with the average full recovery time of 5 seconds. In addition, the good reproducibility of the sensor can be verified by the small relative standard deviation (RSD) of 0.37% for three-time exposure of 100 ppm $C_3H_8$. The calibration curve of $C_3H_8$ is presented in FIG. 6B, which also shows a linear relationship between log|Z| and log $C_{C3H8}$ (concentration of $C_3H_8$).

The sensitive, fast, reversible and reproducible responses of the sensor upon exposure to CO and $C_3H_8$ with excellent selectivity at 800° C. suggest that a high frequency impedancemetric Pt—$CeO_2$ NFs-based sensor is promising for the applications of selective detection of strong reducing gas against oxidizing and weak reducing gas in high temperature harsh environments.

Disclosed herein is the successful fabrication of Pt—$CeO_2$ nanofibers by a facile two-step process (electrospinning followed by calcination). Impedance spectroscopy of the Pt—$CeO_2$ NFs based sensor in varied concentration of $O_2$, CO, $CO_2$, NO, $SO_2$ and $C_3H_8$ was investigated. Equivalent circuit analysis indicates that both the bulk Pt—$CeO_2$ NFs and the interface between sensing material and electrode contributed to the response of the sensor. By plotting the data as Bode plot, it has been shown that reducing gas (CO and $C_3H_8$) can be selectively detected by operating the sensor at a high frequency (100 kHz).

In some embodiments, doping of $CeO_2$ nanofibers is performed with about 5% Pt, in other embodiments of materials for high temperature gas sensors disclosed herein, a broader range of doping with Pt is done between about 0.1% Pt and about 10% Pt.

In other embodiments, doping of $CeO_2$ nanofibers is performed with a suitable metal selected from the group consisting of all Noble metals. In such embodiments, doping may be done in the range of about 0.1% to about 10%, with a preferred range between about 2% and 7%.

In still other embodiments, doped $CeO_2$ nanofibers or doped nanofibers composed of different metal oxides are used as the general basis for an exemplary sensing platform.

In further embodiments, the present disclosure provides for doped nanofibers for fabrication of high temperature selective gas sensors, with the nanofibers including a semiconducting metal oxide selected from the group consisting of a semi-conducting metal oxide (e.g., NiO, $Ga_2O_3$, and others).

In still further embodiments, the present disclosure provides for doped nanofibers for fabrication of high temperature selective gas sensors, with the nanofibers including a pervoskite or pervoskite structure (e.g., LSMO, LSCO and many others).

In certain embodiments, it is noted that the nanofibers disclosed herein may not include or be associated with $Al_2O_3$.

In other embodiments of the exemplary sensor assemblies, the substrate includes materials that, like alumina, are not responsive/reactive with gases at high temperature.

In preferred embodiments of the sensor assemblies disclosed herein, an operating frequency of about 100 kHz is used for detecting both CO and propane. In other embodiments, an operating frequency in the range of about 0.1 Hz to several MHz (e.g., 3 MHz) may be selected depending on the characteristics of the interaction between the sensing materials and the gas species of interest.

In further embodiments of the disclosed technology, the composition of sensor materials and operating conditions may be fine-tuned (e.g., in order to independently measure CO and propane).

The exemplary results included herein indicate that Pt—$CeO_2$ nanofibers are a promising material for the application of high temperature CO and $C_3H_8$ sensors, and that the disclosed impedancemetric technique is a good approach to improve the selectivity of the gas sensors in high temperature environments by tuning the operating frequency.

The present disclosure will be further described with respect to the following examples; however, the scope of the disclosure is not limited thereby. The following examples illustrate, inter alia, the advantageous systems, assemblies and methods of the present disclosure of advantageous sensor assemblies for gases (e.g., high temperature sensor assemblies for reducing gas).

Example 1—Pt—$CeO_2$ Nanofibers Based on High-Frequency Impedancemetric Gas Sensor for Selective CO and $C_3H_8$ Detection in High-Temperature Harsh Environment High-temperature gas sensors are highly demanded to improve the combustion efficiency and reduce the emissions of pollutants. In this disclosure, Pt—$CeO_2$ nanofibers (Pt—$CeO_2$ NFs) were prepared using a two-step synthetic route (electrospinning followed by calcination). The impedance spectroscopy of the Pt—$CeO_2$NFs based sensor was investigated in pure $N_2$ and different gas mixtures ($O_2$, CO, $CO_2$, NO, $SO_2$, and $C_3H_8$ balanced by $N_2$) with various concentrations at 800° C. For the first time, the sensor without a solid electrolyte was operated at high frequency (e.g., about 100 kHz), so that the sensor response towards $O_2$, $CO_2$, NO and $SO_2$ (balanced with $N_2$) was substantially completely eliminated and strong reducing gases (e.g., CO and $C_3H_8$) could be selectively detected with good sensitivity, suggesting that the high-frequency impedancemetric technique is a promising approach to improve the selectivity of high-temperature harsh environment gas sensors when operated at an appropriate frequency.

Introduction:

With increasingly stringent regulation of pollutants, considerable effort has been made to develop high temperature gas sensors to control combustion processes and reduce combustion-related emissions. Incomplete combustion of fossil fuels, which play a dominant role as a primary energy source for automotive and power industries, leads to the emission of carbon monoxide (CO) and hydrocarbons (HCs). In order to improve the combustion efficiency and to reduce the pollutant emission, high temperature CO and hydrocarbons sensors, which can provide real-time feedback to combustion processes and monitor emissions, are highly demanded. On-Board-Diagnostic (OBD) systems usually require the gas sensors to be operated in harsh environment at above 500° C. Specifically, in close proximity to engines, the exhaust gases can reach temperatures close to 1000° C. Therefore, such in-situ applications typically require the gas sensors possessing extremely good thermal stability, as well as high accuracy, sensitivity and selectivity. As a viable and robust technology, ceramic oxide-based electrochemical sensors have received wide interest in high-temperature gas sensing.

Different operating modes for electrochemical sensors have been developed, including amperometric, potentiometric and resistive modes, all of which typically use DC measurements. Most of amperometric and potentiometric electrochemical sensors are based on yttria-stabilized zirconia (YSZ) electrolyte which can be operated at high temperature. Amperometric sensors measure the limited current based on a transport or reaction process, while potentiometric sensors are based upon thermodynamic activity gradients of electrochemically active species between the sensing electrode and the reference electrode. Resistive sensors, possessing a very simple configuration and without using solid electrolyte, measure the resistance change of the sensing material due to the interaction/reaction between the material and analyte gas. However, one of the extreme challenges for current high-temperature gas sensors is the cross-sensitivity of different gases. Researchers have explored a number of strategies (e.g., sensing materials, device configuration, sensing technology, etc.) to improve the selectivity of the gas sensors.

Another electrochemical detection approach, named "impedancemetric," which employs AC measurements at a specified frequency, has drawn lots of attention recently. This approach is related to solid-state impedance spectroscopy which measures the sensor response over a range of frequencies, typically from sub-hertz to megahertz. The impedance spectroscopy is a useful technique to investigate individual electrochemical components based on the frequency-dependent behavior. If the electrochemical components (e.g., electrolyte, interface and bulk material) have significantly different time constant, these components can be separated for individual analysis. Impedancemetric technique based on YSZ has been reported for sensing of water vapor, hydrocarbons, NOx and CO. In addition, this approach also has been applied to the device in the resistor-type configuration without using solid electrolyte YSZ. However, these impedancemetric sensors are operated at low frequency (less than 100 Hz) because the impedance spectra for different concentrations of analyte gas in those studies overlap in the high frequency range and the sensor can only generate distinguishable responses upon exposure to targets at low frequency. Furthermore, the impedancemetric technique for selective high temperature sensor in the resistive configuration is not well investigated.

In this disclosure, novel Pt-decorated $CeO_2$ nanofibers (Pt—$CeO_2$ NFs) were successfully prepared by calcination following electrospinning. It is noted that previous work of the present disclosure has indicated that $CeO_2$ possesses excellent thermal stability up to 1000° C. which is one of the most promising materials for high-temperature gas sensor application. However, a $CeO_2$-based resistor-type high-temperature gas sensor responds to reducing gas and oxidizing gas in the opposite direction, which may result in poor selectivity and inaccuracy of measured gas concentration. In this disclosure, it is demonstrated that an impedancemetric high-temperature gas sensor, operating at a high frequency (100 kHz), can substantially completely eliminate the response from substantially all tested oxidizing gas and weak reducing gas (e.g., $O_2$, $CO_2$, NO and $SO_2$ balanced with $N_2$) and selectively detect strong reducing gas (e.g., CO and $C_3H_8$ balanced with $N_2$) with ultra-high sensitivity and excellent reproducibility. With Pt doping, the $CeO_2$ sensing material can achieve better catalytic performance towards CO and $C_3H_8$, which can improve the sensing performance. The Pt—$CeO_2$ NFs based sensor was fabricated without using solid electrolyte, which is simple and cost-effective. The impedance spectra of six gases (CO, $O_2$, $SO_2$, NO, $CO_2$ and $C_3H_8$) at varied concentrations were measured at 800° C. and the equivalent circuit analysis was conducted to understand the sensing mechanism. The results suggest that the high-frequency impedancemetric approach of the present disclosure is a promising technique to improve the selectivity of harsh environment gas sensors.

Experimental:

Reagents:

Cerium(III) nitrate hexahydrate ($Ce(NO_3)_3.6H_2O$), hydrogenhexachloroplatinate (IV) hexahydrate ($H_2PtCl_6.6H_2O$, 99.90%) and dimethylformamide (DMF) were purchased from Acros Organics. Poly(vinyl pyrrolidone) (PVP, MW=1,300,000) was obtained from Sigma-Aldrich. For gas sensing studies, high purity nitrogen ($N_2$, 99.998%), $O_2/N_2$ gas mixtures (97 ppm $O_2$ or 10% $O_2$ in $N_2$), CO/Ar gas mixture (1% CO in Ar), high purity $CO_2$ (99.998%), $NO/N_2$ gas mixture (500 ppm NO in $N_2$) and $SO_2/N_2$ gas mixture (253 ppm $SO_2$ in $N_2$) were ordered from Airgas.

Preparation of Pt—$CeO_2$ NFs:

By incorporating metal salts into polymer, noble metal-ceramic nanofibers can be fabricated by a two-step procedure which consists of electrospinning and a subsequent calcination process. To prepare the precursory solution for Pt—$CeO_2$, the total weight of 0.386 g metal salts (the molar percentage of Pt is 5%) were dissolved in 3 mL DMF and then 0.386 g PVP was added, followed by stirring. The final homogeneous mixture was loaded into a plastic syringe with a 23-gauge needle for electrospinning. The $H_2PtCl_6$—$Ce(NO_3)_3$-PVP precursory nanofibers were fabricated by electrospinning with a flow rate of 0.3 mL/h at an applied voltage of 20 kV over a collection distance of 15 cm. The precursor nanofibers were then calcined in air following two steps. First, the as-spun sample was calcined at 500° C.

for 3 hours in order to remove the matrix polymer and generate Pt—$CeO_2$ NFs. This step provided good morphology of Pt—$CeO_2$ NFs. Due to an exemplary target sensing operation temperature of 800° C., the Pt—$CeO_2$ NFs (calcined at 500° C.) were further calcined at 1000° C. for 3 hours to improve the crystal structure and thermal stability, which were then employed as sensing material for subsequent gas detection.

Characterization of Pt—$CeO_2$ NFs:

A JEOL 6335F field-emission scanning electron microscope (SEM) was employed to examine the morphology and the size of the as-electrospun Pt—$CeO_2$ NFs after two-step calcination. Energy dispersive X-ray spectrometer (EDX) attached with the SEM was used to characterize the composition of calcined nanofibers. The crystal structure and the composition of the sample were further characterized by Oxford diffraction Xcalibur™ PX Ultra with ONYX detector.

Sensor Device Fabrication:

The resistor-type Pt—$CeO_2$ NFs based sensor was fabricated on an $Al_2O_3$ ceramic screw (4-40×½"), as illustrated in FIG. 2A. Two Pt wires, serving as two electrodes, were tightly tied onto the two close threads of the ceramic screw which acts as the substrate. The as-prepared Pt—$CeO_2$ NFs were suspended in ethanol and sonicated for 30 minutes, and then the suspension was casted onto the substrate and covered the two Pt electrodes, thus completing the fabrication of the sensing device. The sensor was connected to a CHI 660D electrochemical analyzer (CH Instruments Inc., USA) through two long Ni—Cr alloy wires and was placed in the center of a furnace with a temperature control to conduct in-situ high temperature gas sensing.

Impedance Spectroscopy:

Impedance spectra of the Pt—$CeO_2$ NFs based sensor in $N_2$ and different gas mixtures were measured by CHI in the frequency range 0.1 Hz to 1 MHz with an amplitude of 0.5 V at 800° C. High purity nitrogen was used as balanced gas to obtain various concentrations of test gases, including $O_2$, CO, $CO_2$, NO, $SO_2$ and $C_3H_8$. The sensor was subjected to a gas flow with a constant flow rate of 1.5 L/min, which were regulated by a computer-controlled gas mixing system (S-4000, Environics Inc., USA). The equivalent circuit analysis was conducted by CHI simulation software.

Real-Time Gas Sensing at High Temperature:

The performance of the Pt—$CeO_2$ NFs based gas sensor at 800° C. was evaluated by measuring the impedance modulus |Z| change upon exposure to various concentrations of different gas mixtures in a dynamic gas flow system with a constant gas flow rate of 1.5 L/min. At 800° C., strong reducing gas (e.g., CO and $C_3H_8$) could react with $O_2$, therefore, high purity nitrogen was used as the carrying gas instead of air. In a typical CO sensing experiment, the sensor placed in a furnace at 800° C. was first exposed to CO/$N_2$ mixture for 5 minutes, followed by high purity $N_2$ for 10 minutes to recover the sensor, and then the "exposure/recovery" cycle was repeated. Except for propane, the other gas sensing experiments used high purity $N_2$ as recovering gas. Due to the strong reducing ability of propane, the sensor cannot be fully recovered by $N_2$, therefore, 1% $O_2$ was used as recovering gas in propane detection. Due to the fast recovery by 1% $O_2$, the recovery time in propane detection was set for 5 minutes. The impedance of the sensor was continuously measured at a fixed frequency of 100 kHz with amplitude of 0.5 V.

Results and Discussion:

Material Characterization:

After calcined at 500° C. for 3 hours, the morphology of Pt—$CeO_{2(500)}$ NFs was characterized by SEM, as shown in FIG. 1A. The nanofibers were uniform and well-distributed with an average diameter of 177±17 nm. After calcination at 1000° C. for another 3 hours, the average diameter of the nanofibers slightly shrank to 138±14 nm, and compared to the smooth surface of Pt—$CeO_{2(500)}$ NFs, a few nanoparticles with an average diameter of 85±25 nm emerged on the surface of the Pt—$CeO_{2(1000)}$ NFs. The X-ray energy dispersive spectroscopy (EDX) point analysis was employed to investigate the compositions of the nanofibers and nanoparticles on the surface. FIG. 1C presents the EDX spectrum on one point of a randomly selected Pt—$CeO_{2(1000)}$ NFs, indicating the presence of Ce, Pt and oxygen in the nanofiber matrix. On the contrary, from the point EDX spectrum of a randomly selected nanoparticle on the Pt—$CeO_2$ NFs (FIG. 1D), one can see that the nanoparticles on the nanofibers surface are mainly composed of Pt. These results imply that some of the Pt can migrate from the nanofibers to the surface and thus form Pt nanoparticles during the calcination process at 1000° C., which is also partially responsible for the reduced diameter of the nanofibers. XRD was carried out to further characterize the composition and crystal structure of the as-prepared Pt—$CeO_{2(1000)}$ NFs. As shown in FIG. 1E, the XRD spectrum of Pt—$CeO_2$ NFs matches the combination of the standard spectra of $CeO_2$ and Pt, which revealed the formation of $CeO_2$ and Pt after calcination.

Impedance Spectra and Equivalent Circuit Analysis:

The as-prepared Pt—$CeO_{2(1000)}$ NFs were then employed as the sensing material to fabricate the sensor on an $Al_2O_3$ ceramic screw as described before. Complex impedance measurement was first performed on the Pt—$CeO_2$ NFs-based sensor. FIGS. 2C and D show the Nyquist plots (data dots) obtained from the sensor at 800° C. in high purity $N_2$ and in the gas mixture with different concentrations of $O_2$ and CO balanced by $N_2$. One can see from FIG. 2C that a large and slightly depressed semicircular arc with a small tail can be observed in $N_2$, as well as in different concentrations of $O_2$ mixtures in the examined frequency range (0.1 Hz to 1 MHz). With increasing concentrations of $O_2$, the radius of the semi-circular arc greatly increased, implying that the sensor is sensitive to $O_2$. The impedance spectra in different concentrations of $SO_2$, $CO_2$ and NO were also measured, which are very similar to the one of $N_2$, as shown in FIG. 7A. $CO_2$ and NO showed weak oxidizing property, while $SO_2$ exhibited a weak reducing behavior; and the sensor showed response towards these three gases to certain degree. From FIG. 2D, one can notice that the impedance magnitude |Z| of the sensor in CO/$N_2$ mixture dramatically dropped by 2 orders of magnitude and the shape of the impedance spectra also shrank to only a portion of the semicircular arc, indicating that CO is a strong reducing gas and the Pt—$CeO_2$ NFs is extremely sensitive to CO.

Equivalent circuit analysis was conducted to better understand the response mechanism. FIG. 2B presents the equivalent circuit model for the Pt—$CeO_2$ NFs-based sensor. A RC-parallel element ($R_1 \| C_1$) corresponds to the bulk Pt—$CeO_2$ NFs. $R_1$ represents the resistance of bulk Pt—$CeO_2$ NFs and $C_1$ is related to the dielectric properties of the material. The following element (($R_2 \| CPE_1$)+$CPE_2$) in series was used to describe the interface between sensing material and Pt electrodes. $R_2$ represents the charge transfer resistance at the interface. A constant phase element $CPE_1$ was used to account for the non-ideal behavior of the double layer at the interface due to the porosity, surface roughness, etc. The low-frequency Warburg-like contribution was described by $CPE_2$, which is associated with gas diffusion. To accomplish the model, a parallel capacitor ($C_0$) is applied to stand for the capacity of $Al_2O_3$ substrate. Because the time constants of RC-parallel element ($R_1 \| C_1$) and RQ-parallel element ($R_2 \| CPE_2$) are close to each other, they both contribute to the large arc. The small tail following the large arc can be ascribed to gas diffusion, corresponding to $CPE_2$. The value of $C_0$ was pre-determined by simulation of the device without $Pt$—$CeO_2$ NFs, which is $1 \times 10^{-11}$ F. Based on the reports on double layer capacitance, the dielectric constants in the double-layers have roughly the same value with varied concentration of oxygen vacancies. Therefore, $n_1$ in $CPE_1$, which is related to the dielectric constants in the double layer capacitance, was also set as a constant of 0.8 to fit the experimental data due to the large number of variables. For the diffusion related $CPE_2$ which is responsible for the tail in low frequency range, $n_2$ was set as constant of 0.1 except the cases of $O_2$ with different concentrations. Under these pre-selected constants, this equivalent circuit model gives a very good approximation of the experimental results. As shown in FIGS. 2C and 2D, the solid lines are the fitting curves which are in a good agreement with the experiment data points. The parameters of the model for the fitting curves in different gas atmospheres are listed in Table S1. From the fitting parameters in Table S1, it is concludes that both of the resistance of bulk $Pt$—$CeO_2$ NFs ($R_1$) and the interface charge transfer resistance ($R_2$) are the two major contributors to the change of the impedance spectra. In addition, the sum of the fitting values of $R_1$ and $R_2$ is very close to the measured resistance of the sensor device in different gas atmosphere (which can be presented as the diameter of the large arc), further indicating the reliability of the fitting values in equivalent circuit model and appropriateness of the pre-selected constant values. $CeO_2$ is an n-type semiconductor and the predominant point defects in $CeO_2$ are the electron trapped by lattice Ce and oxygen vacancy. The reaction for the formation of ionic and electronic charge carriers can be written as Equation 1 above.

Upon the exposure to $O_2$, oxygen can incorporate with electrons and oxygen vacancy to form lattice oxygen, leading to the increased resistance $R_1$ and reduced capacitance $C_1$. It was reported that the capacitance of $CeO_2$ decreases with increasing oxygen partial pressure, which is in a good agreement with the fitting data. After introducing CO to the gas atmosphere, CO could extract lattice oxygen to form $CO_2$ and generate oxygen vacancies and electrons according to Equation 1. Due to the increasing concentration of electrons, both material bulk resistance $R_1$ and charge transfer resistance $R_2$ dramatically decrease. The oxygen depletion also results in an increase in the capacitance $C_1$. For the low-frequency Warburg-like contribution $CPE_2$, with increasing concentration of $O_2$, $n_2$ increased from 0.11 to 0.24, suggesting that the diffusion of $O_2$ plays an important role at low frequency with more capacitor effect. This can also be verified by the longer tail of the impedance spectrum at higher $O_2$ concentration. The fitting parameters of weak oxidizing gas $CO_2$ and NO showed the same trend as $O_2$, while weak reducing gas $SO_2$ behaved like CO.

Improved Selectivity at High Frequency:

The impedance spectroscopy data of the sensor in different gas atmospheres can be also presented as Bode plots, where log|Z| is plotted vs. log (frequency), as shown in FIG. 3. In all cases, with decreasing frequency, the modulus |Z| of the sensor increased and gradually reached their plateau. For 100 ppm CO, |Z| almost kept as a constant in the examined frequency range. For the impedancemetric real-time gas detection, the frequency has to be fixed, which can be selected based on the Bode plots. In Bode plots, take the spectrum of $N_2$ as the baseline (black square), the larger the distance is between the targeted gas and $N_2$, the more sensitive the sensor is towards that targeted gas. One can see from FIG. 3 that, in low frequency range, the sensor is sensitive to $O_2$ with increasing modulus and CO with reducing modulus, and it also shows concentration-dependent behavior for all tested gases. In the high frequency range (greater than 10 kHz), except $CO/N_2$ mixture, the Bode plots for all other tested gases at different concentrations overlapped, indicating that the sensor is only sensitive to strong reducing gas CO and it has almost no response towards the concentration change of other tested gases, and thus provide enhanced selectivity. However, with increasing frequency (10 kHz to 1 MHz), the sensor response towards CO also decreases compared to that at low frequency. In order to achieve the good selectivity while maintaining good sensitivity towards CO, the optimized operating frequency was selected at 100 kHz.

$Pt$—$CeO_2$ NFs based DC resistor-type sensor was also tested in order to verify the enhanced selectivity of the impedancemetric sensor operated at high frequencies. High purity $N_2$ was used as the reference gas. Because both the resistance (for DC resistor-type sensor) and the impedance modulus (for impedancemetric sensor) changes in several orders and in different directions for $O_2$ and CO, the sensitivity of the impedancemetric sensor is defined as $\log(Z_g/Z_0)$, where $Z_g$ is the real-time measured modulus upon exposure to different gas mixture and $Z_0$ is the initial modulus in high purity $N_2$; and similarly, the sensitivity of the DC resistor-type sensor is defined as $\log(R_g/R_0)$. The real-time selectivity study used $O_2$ and $CO_2$, as demonstration. As shown in FIGS. 4A and 4B, for the DC resistor-type sensor, 1% $O_2$ introduced 33% interference to the response of 100 ppm CO, while for impedancemetric sensor operated at 100 kHz, $O_2$ only showed negligible response. The real-time detection of $CO_2$, NO and $SO_2$ were also performed. At the selected frequency, the sensor barely showed any response towards these gases. The selectivity of $Pt$—$CeO_2$ NFs based impedancemetric sensor and DC resistor-type sensor towards different gases is summarized in FIG. 4C using the absolute normalized response for different gases (on the basis of the response to 100 ppm CO). As presented in FIG. 4C, the DC resistor-type sensor suffers from significant interference from high concentration of oxygen and other gaseous species, while the impedance sensor exhibited good selectivity towards CO at the selected operating frequency of 100 kHz, suggesting that the developed impedancemetric sensor operated at high frequencies is a promising sensor towards selective detection of strong reducing gas in high-temperature harsh environments.

Real-Time CO Detection:

The real-time CO detection of $Pt$—$CeO_2$ NFs-based impedance-metric sensor was carried out at high operating temperature of 800° C. with a fixed frequency of 100 kHz. FIG. 5A represents typical impedance modulus responses of the sensor as a function of time upon periodic exposure to CO (with concentrations from 20 ppm to 100 ppm) balanced by high purity $N_2$. The sensor showed good sensitivity at the operating frequency of 100 kHz towards CO. Upon exposure to 100 ppm CO, the modulus of the sensor quickly drops and is 10 times smaller than the |Z| in $N_2$. The response time ($t_{90}$) of the sensor towards 100 ppm CO is 50 seconds, which is defined as the time when the change of |Z| reached 90% of the maximum response after exposure to CO. The actual response time should be much faster considering the time required for the gas to fill the test chamber. The response of the sensor towards CO can be completely recovered by $N_2$ and the sensor responses towards three-time exposure of 100 ppm CO showed good reproducibility with a small relative standard deviation (RSD) of 0.5%. A comparison study of the DC resistor-type sensor fabricated with $CeO_2$ NFs indicates that the presence of Pt in Pt—$CeO_2$ NFs could significantly improve the sensing performance towards CO detection, which can be ascribed to strong catalytic activity of Pt. It was reported that, with the doping of Pt, Pt/$CeO_2$ can be more easily reduced by CO than pure $CeO_2$. The response of Pt—$CeO_2$ NFs towards 50 ppm CO is almost three-fold that of $CeO_2$ NFs, as shown in FIG. 8. The CO concentration dependent behavior was revealed by the calibration curve presented in FIG. 5B, which shows a linear relationship between log|Z| and log $C_{CO}$ (CO concentration).

Real-Time $C_3H_8$ Detection:

To further verify the idea, $C_3H_8$, another strong reducing gas from the hydrocarbon group, was tested. Impedance spectra of the Pt—$CeO_2$ NFs-based sensor towards different concentration of $C_3H_8$ balanced by $N_2$ were first measured. Nyquist plots were shown in FIG. 7B which only exhibits very short curves for 80 ppm and 100 ppm $C_3H_8$, indicating that the sensor is even more sensitive to $C_3H_8$ than to CO. FIG. 6A shows the Bode plots for three concentrations of $C_3H_8$, pure $N_2$ and 1% $O_2$ (for other gases, cf. FIG. 3). At 100 kHz, the sensor showed good sensitivity towards $C_3H_8$ and no response towards $O_2$ concentration change. Due to the strong reducing property of $C_3H_8$, the sensor cannot be fully recovered by high purity $N_2$. Therefore, 1% $O_2$ was chosen as recovering gas, since there is no difference of the baseline in pure $N_2$ and 1% $O_2$. FIG. 6B presents the real-time $C_3H_8$ detection at an operating frequency of 100 kHz at 800° C. The sensor exhibited excellent sensitivity towards 100 ppm $C_3H_8$, demonstrated by the fact that the impedance modulus of the sensor quickly drops 30 times compared to the modulus in 1% $O_2$. The recovery of the sensor from exposure to $C_3H_8$ by 1% $O_2$ is very fast with an average recovery time of 5 seconds. In addition, the good reproducibility of the sensor can be verified by the small relative standard deviation (RSD) of 0.37% for three-time exposure of 100 ppm $C_3H_8$. The calibration curve of $C_3H_8$ was presented in FIG. 6B, which also shows a linear relationship between log|Z| and log $C_{C3H8}$ ($C_3H_8$ concentration). The sensitive, fast, reversible and reproducible responses of the sensor upon exposure to CO and $C_3H_8$ with excellent selectivity at 800° C. suggest that high frequency impedancemetric Pt—$CeO_2$ NFs-based sensors are promising for selective detection of strong reducing gases against oxidizing and weak reducing gases in high-temperature harsh environments. To further differentiate gases in the group of strong reducing gas which is very challenging, more work may be completed.

Conclusions:

In conclusion, the present disclosure provides for fabricated Pt—$CeO_2$ NFs by a facile two-step process (electrospinning followed by calcination). Impedance spectroscopy of the Pt—$CeO_2$ NFs based sensor in different concentrations of $O_2$, CO, $CO_2$, NO, $SO_2$ and $C_3H_8$ was investigated. Equivalent circuit analysis indicates that both the bulk Pt—$CeO_2$ NFs and the interface between sensing material and electrode contributed to the major response of the sensor. By plotting the data as Bode plots, it was realized that strong reducing gas (CO and $C_3H_8$) can be selectively detected by operating the sensor at a high frequency (e.g., 100 kHz). These good results indicate that Pt—$CeO_2$ NFs are a promising material for the application of high-temperature CO and $C_3H_8$ sensors and the impedancemetric technique is a good approach to improve the selectivity of gas sensors in high-temperature environments by tuning the operating frequency.

TABLE S1

The fitting parameters of Pt—$CeO_2$ NFs based sensor in equivalent circuit model($C_0 = 1 \times 10^{-11}$ F, $n_1 = 0.8$)

| | Concentration | $R_1/\Omega$ | $C_1/F$ | $R_2/\Omega$ | $Q_1$ | $Q_2$ | $n_2$ |
|---|---|---|---|---|---|---|---|
| $O_2$ | 500 ppm | $7.17 \times 10^5$ | $1.31 \times 10^{-11}$ | $7.09 \times 10^5$ | $3.13 \times 10^{-10}$ | $2.79 \times 10^{-5}$ | 0.11 |
| | 1% | $1.09 \times 10^6$ | $1.22 \times 10^{-11}$ | $1.10 \times 10^6$ | $3.31 \times 10^{-10}$ | $1.33 \times 10^{-5}$ | 0.16 |
| | 10% | $1.79 \times 10^6$ | $1.18 \times 10^{-11}$ | $1.26 \times 10^6$ | $3.23 \times 10^{-10}$ | $4.35 \times 10^{-6}$ | 0.24 |
| NO | 10 ppm | $3.63 \times 10^5$ | $1.35 \times 10^{-11}$ | $3.37 \times 10^5$ | $2.86 \times 10^{-10}$ | $4.08 \times 10^{-5}$ | 0.1 |
| | 1000 ppm | $3.96 \times 10^5$ | $1.34 \times 10^{-11}$ | $3.75 \times 10^5$ | $2.84 \times 10^{-10}$ | $4.24 \times 10^{-5}$ | 0.1 |
| $CO_2$ | 10-30% | $3.76 \times 10^5$ | $1.34 \times 10^{-11}$ | $3.51 \times 10^5$ | $2.85 \times 10^{-10}$ | $4.53 \times 10^{-5}$ | 0.1 |
| $N_2$ | 100% | $3.48 \times 10^5$ | $1.41 \times 10^{-11}$ | $3.27 \times 10^5$ | $2.68 \times 10^{-10}$ | $4.75 \times 10^{-5}$ | 0.1 |
| $SO_2$ | 30 ppm | $3.22 \times 10^5$ | $1.36 \times 10^{-11}$ | $2.87 \times 10^5$ | $2.86 \times 10^{-10}$ | $4.62 \times 10^{-5}$ | 0.1 |
| | 75 ppm | $3.08 \times 10^5$ | $1.36 \times 10^{-11}$ | $2.60 \times 10^5$ | $2.87 \times 10^{-10}$ | $4.26 \times 10^{-5}$ | 0.1 |
| CO | 20 ppm | $1.74 \times 10^4$ | $1.65 \times 10^{-11}$ | $9.32 \times 10^3$ | $9.98 \times 10^{-12}$ | $9.46 \times 10^{-4}$ | 0.1 |
| | 50 ppm | $5.54 \times 10^3$ | $2.77 \times 10^{-11}$ | $6.74 \times 10^3$ | $9.62 \times 10^{-12}$ | $6.58 \times 10^{-2}$ | 0.1 |
| | 100 ppm | $1.02 \times 10^3$ | $1.58 \times 10^{-10}$ | $5.67 \times 10^3$ | $8.49 \times 10^{-12}$ | $1.92 \times 10^{-2}$ | 0.1 |

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. An impedancemetric sensor assembly comprising:
   a substrate;
   one or more electrodes positioned on the substrate;

a plurality of electrospun nanofibers positioned on the substrate;
wherein the impedancemetric sensor assembly is adapted to operate at a temperature of about 500° C. or more and a fixed frequency of about 100 kHz or more, and
wherein the sensor assembly generates a real-time impedance value at the fixed frequency to detect a gas.

2. The assembly of claim 1, wherein the detected gas is CO or $C_3H_8$.

3. The assembly of claim 1, wherein the impedancemetric sensor assembly is adapted to operate at a temperature of from about 800° C. to about 1000° C. to detect the gas.

4. The assembly of claim 1, wherein the impedancemetric sensor assembly is adapted to operate at a frequency of from about 100 kHz to about 1 MHz to detect the gas.

5. The assembly of claim 1, wherein the impedancemetric sensor assembly is adapted to operate to provide real-time detection of the gas.

6. The assembly of claim 1, wherein the plurality of electrospun nanofibers include $Pt$—$CeO_2$ nanofibers.

7. The assembly of claim 1, wherein the plurality of electrospun nanofibers are configured and adapted to have high thermal stability and the impedancemetric sensor assembly has high sensitivity toward strong reducing gases.

8. The assembly of claim 2, wherein there is substantially no interference from $O_2$, $CO_2$, NO or $SO_2$ at the operating frequency selected for detection of CO or $C_3H_8$.

9. The assembly of claim 1, wherein the impedancemetric sensor assembly is adapted to operate in a dynamic flow system to detect the gas.

10. The assembly of claim 1, wherein the plurality of electrospun nanofibers include $CeO_2$ nanofibers doped with material selected from the group consisting of noble metals, metal oxides, semi-conducting metal oxides, pervoskites, pervoskite structures and combinations thereof.

11. A method for fabricating an impedancemetric sensor assembly comprising:
 a) providing a substrate;
 b) positioning one or more electrodes on the substrate;
 c) positioning a plurality of electrospun nanofibers on the substrate to form a sensing assembly;
 d) operating the sensing assembly at a temperature of about 500° C. or more and a fixed frequency of 100 kHz or more to generate a real-time impedance value at the fixed frequency to detect a gas.

12. The method of claim 11, wherein prior to step c), the plurality of electrospun nanofibers are fabricated by: (i) electrospinning $H_2PtCl_6$—$Ce(NO_3)_3$-PVP precursor nanofibers, and (ii) calcinating the electrospun precursor nanofibers to generate a plurality of electrospun $Pt$—$CeO_2$ nanofibers.

13. The method of claim 12, wherein calcinating the electrospun precursor nanofibers includes: (i) calcinating the electrospun precursor nanofibers during a first calcination step at about 500° C. for about 3 hours, and (ii) calcinating the electrospun precursor nanofibers during a second subsequent calcination step at about 1000° C. for about 3 hours to generate the plurality of electrospun $Pt$—$CeO_2$ nanofibers.

14. The method of claim 11, wherein the detected gas is CO or $C_3H_8$.

15. The method of claim 11, wherein the impedancemetric sensor assembly is operated at a temperature of from about 800° C. to about 1000° C. to detect the gas.

16. The method of claim 11, wherein the impedancemetric sensor assembly is operated at a frequency of from about 100 kHz to about 1 MHz to detect the gas.

17. The method of claim 11, wherein the plurality of electrospun nanofibers include $Pt$—$CeO_2$ nanofibers.

18. The method of claim 11, wherein the plurality of electrospun nanofibers include $CeO_2$ nanofibers doped with material selected from the group consisting of noble metals, metal oxides, semi-conducting metal oxides, pervoskites, pervoskite structures and combinations thereof.

19. A method for detecting a gas, comprising:
 a. providing a sensor assembly that that includes (i) a substrate, (ii) one or more electrodes positioned on the substrate, and (iii) a plurality of electrospun nanofibers on the substrate to form the sensor assembly;
 b. operating the sensor assembly at a temperature of about 500° C. or more and a fixed frequency of 100 kHz or more to generate a real-time impedance value at the fixed frequency to detect the gas.

20. The method of claim 19, wherein the detected gas is CO or $C_3H_8$.

21. The method of claim 19, wherein the plurality of electrospun nanofibers are selected from the group consisting of (i) $Pt$—$CeO_2$ nanofibers, and (ii) $CeO_2$ nanofibers doped with material selected from the group consisting of noble metals, metal oxides, semi-conducting metal oxides, pervoskites, pervoskite structures and combinations thereof.

22. The method of claim 19, wherein there is substantially no interference from $O_2$, $CO_2$, NO or $SO_2$ at the operating frequency selected for detection of CO or $C_3H_8$.

* * * * *